(12) United States Patent
Sandino et al.

(10) Patent No.: US 11,823,307 B2
(45) Date of Patent: Nov. 21, 2023

(54) METHOD FOR HIGH-DIMENSIONAL IMAGE RECONSTRUCTION USING LOW-DIMENSIONAL REPRESENTATIONS AND DEEP LEARNING

(71) Applicant: The Board of Trustees of the Leland Stanford Junior University, Stanford, CA (US)

(72) Inventors: Christopher Michael Sandino, Menlo Park, CA (US); Shreyas S. Vasanawala, Stanford, CA (US); Frank Ong, Palo Alto, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 154 days.

(21) Appl. No.: 17/319,316

(22) Filed: May 13, 2021

(65) Prior Publication Data
US 2022/0375141 A1 Nov. 24, 2022

(51) Int. Cl.
*G06K 9/00* (2022.01)
*G06T 11/00* (2006.01)
(Continued)

(52) U.S. Cl.
CPC ............ *G06T 11/006* (2013.01); *G06T 7/11* (2017.01); *A61B 5/055* (2013.01); *G06T 2207/10088* (2013.01); *G06T 2207/20021* (2013.01)

(58) Field of Classification Search
CPC .............. G06T 11/006; G06T 7/11; G06T 2207/10088; G06T 2207/20021;
(Continued)

(56) References Cited

U.S. PATENT DOCUMENTS 10,436,871 B2 10/2019 Li
10,712,416 B1 7/2020 Sandino
(Continued)

OTHER PUBLICATIONS

Lustig & Pauly, "SPIRIT: Iterative Self-consistent Parallel Imaging Reconstruction from Arbitrary k-Space", Published Aug. 2010 (Year: 2010).*

(Continued)

*Primary Examiner* — Alex Kok S Liew
(74) *Attorney, Agent, or Firm* — LUMEN PATENT FIRM (57) ABSTRACT

A method for MR imaging includes acquiring with an MR imaging apparatus undersampled k-space imaging data having one or more temporal dimensions and two or more spatial dimensions; transforming the undersampled k-space imaging data to image space data using zero-filled or sliding window reconstruction and sensitivity maps; decomposing the image space data into a compressed representation comprising a product of spatial and temporal parts, where the spatial part comprises spatial basis functions and the temporal part comprises temporal basis functions; processing the spatial basis functions and temporal basis functions to produce reconstructed spatial basis functions and reconstructed temporal basis functions, wherein the processing iteratively applies conjugate gradient and convolutional neural network updates using 2D or 3D spatial and 1D temporal networks; and decompressing the reconstructed spatial basis functions and reconstructed temporal basis functions to produce a reconstructed MRI image having one or more temporal dimensions and two or more spatial dimensions.

3 Claims, 5 Drawing Sheets

(51) Int. Cl.
    *G06T 7/11*      (2017.01)
    *A61B 5/055*     (2006.01)

(58) Field of Classification Search
    CPC . G06T 2207/20084; G06T 2207/20081; G06T 11/008; G06T 2210/41; G06T 5/002; G06T 7/0012; G06T 11/005; G06T 2207/20224; G06T 2207/30016; G06T 2207/20056; G06T 2207/20182; G06T 7/262; G06T 2207/20216; G06T 3/60; G06T 2211/424; G06T 7/38; G06T 7/0014; G06T 2207/10076; G06T 2207/10081; G06T 2207/10084; A61B 5/055; A61B 5/0515; G06N 3/045; G06N 3/08; G06N 3/084; G06N 3/088; G06N 7/01; G06N 3/082; G06N 3/04; G06N 3/02; G06N 20/00; G06N 3/0464; G06N 20/20

See application file for complete search history.

(56) References Cited

U.S. PATENT DOCUMENTS

| | | | |
|---|---|---|---|
| 10,832,451 B2* | 11/2020 | Demesmaeker | G06N 3/08 |
| 2017/0309019 A1 | 10/2017 | Knoll | |
| 2019/0059780 A1* | 2/2019 | Lee | A61B 5/7264 |

OTHER PUBLICATIONS

Zhang et al, "Fast Pediatric 3D Free-breathing Abdominal Dynamic Contrast Enhanced MRI with High Spatiotemporal Resolution" Journal of Magnetic Resonance Imaging, Published Feb. 2015 (Year: 2015).*

Sandino et al. "Accelerating cardiac cine MRI using a deep learning-based ESPIRiT reconstruction", arXiv document No. 1911.05845v2, published online Mar. 10, 2020 (Year: 2020).*

Sandino, et al., "Accelerating cardiac cine MRI using a deep learning-based ESPIRiT reconstruction," Magnetic Resonance in Medicine, vol. 85, pp. 152-167, Jan. 2021.

Ong, et al., "Extreme MRI: Large-Scale Volumetric Dynamic Imaging from Continuous Non-Gated Acquisitions," arXiv:1909.13482 [physics], Sep. 2019.

* cited by examiner

Fig. 1A $$X = LR^H$$

Fig. 1B $$X = \sum_{b=1}^{N} M_b(L_b R_b^H)$$

*Fig. 1C*

| 150 acquiring with an MRI imaging apparatus undersampled k-space imaging data having one or more temporal dimensions and two or more spatial dimensions |
|---|

↓

| 152 transforming the undersampled k-space imaging data to image space data using zero-filled or sliding window reconstruction and sensitivity maps |
|---|

↓

| 154 decomposing the image space data into a compressed representation comprising a product of spatial and temporal parts, where the spatial part comprises spatial basis functions and the temporal part comprises temporal basis functions |
|---|

↓

| 156 processing the spatial basis functions and temporal basis functions to produce reconstructed spatial basis functions and reconstructed temporal basis functions, wherein the processing iteratively applies conjugate gradient and convolutional neural network updates using 2D or 3D spatial and 1D temporal networks |
|---|

↓

| 158 decompressing the reconstructed spatial basis functions and reconstructed temporal basis functions to produce a reconstructed MRI image having one or more temporal dimensions and two or more spatial dimensions |
|---|

METHOD FOR HIGH-DIMENSIONAL IMAGE RECONSTRUCTION USING LOW-DIMENSIONAL REPRESENTATIONS AND DEEP LEARNING

STATEMENT REGARDING FEDERALLY SPONSORED RESEARCH OR DEVELOPMENT

This invention was made with Government support under contract EB026136 awarded by the National Institutes of Health, and under contract EB009690 awarded by the National Institutes of Health. The Government has certain rights in the invention.

FIELD OF THE INVENTION

The present invention relates generally in magnetic resonance imaging (MRI). More specifically, it relates to techniques for MRI image reconstruction using deep learning.

BACKGROUND OF THE INVENTION

Magnetic resonance imaging (MRI) conventionally uses methods such as parallel imaging and compressed sensing (PICS) to reconstruct images from undersampled data and enable highly accelerated scan times [1-3]. These methods typically use iterative reconstruction to estimate missing information in the undersampled data.

Recently, deep neural networks (DNNs) have been shown to outperform conventional iterative methods for MRI image reconstruction tasks [4, 5]. Not only can they produce images with better image quality than PICS, but they also reconstruct images at a much faster rate by leveraging optimized DNN libraries on a graphics processing unit (GPU). However, DNNs must be trained on historical MRI data to learn how to reconstruct an image. This is often done by training the network with examples of undersampled inputs and fully-sampled targets. The DNN weights are then optimized through a stochastic training process which iteratively minimizes the loss computed between the DNN output and fully-sampled target. This training process often requires large amounts of memory, and available memory places limits on the spatial and temporal resolution of the data used to train DNNs. Moreover, available memory also limits the applications of DNN-based reconstruction to only lower-dimensional MR imaging data (i.e. 2D and 3D). Higher-dimensional MRI techniques have memory requirements which are beyond the capabilities of modern day GPU hardware.

BRIEF SUMMARY OF THE INVENTION

To address this issue, the present inventors have developed a technique called deep subspace learning reconstruction (DSLR). The technique provides:
1. A method for converting incomplete, high-dimensional sensor data into a compressed representation which leverages low-rank structure in the data.
2. A method for using DNNs to reconstruct data in the compressed domain. This method uses simpler neural networks (2D and 1D) to reconstruct high-dimensional data (3D, 4D, 5D, etc.) allowing for memory-efficient training and inference.
3. A method for integrating MRI physics-based modeling to constrain the compressed representation of the data during reconstruction (also known as data consistency).
4. A method for de-compressing the compressed representations at the very end of the reconstruction when it is time to visualize images.

In contrast to other DNN-based image reconstruction techniques, DSLR can be trained to reconstruct similar quality images at a lower computational cost as a result of leveraging a compressed representation during the reconstruction.

Embodiments of the invention can be used for any magnetic resonance imaging scans that are subsampled. It can be especially useful for imaging applications that attempt to resolve data with three spatial dimensions (x, y, z) in addition to various temporal dimensions (e.g., dynamic contrast-enhanced imaging, 3D cardiac cine, 4D Flow, multi-contrast imaging, diffusion imaging). Not only does this technique make the use of neural networks for high-dimensional image reconstruction tractable, but it also reduces the computational complexity of the reconstruction since the target data is the compressed representation, and not the full data itself.

Techniques of this invention are applicable across other types of imaging both medical and non-medical including: computed tomography, positron emission tomography, optical microscopy, etc. Generally, these techniques can be applied to any type of imaging that requires solving a least-squares inverse problem to reconstruct images from the raw sensor data.

In one aspect, the invention provides a method for MR imaging. The method includes: acquiring with an MR imaging apparatus undersampled k-space imaging data having one or more temporal dimensions and two or more spatial dimensions; transforming the undersampled k-space imaging data to image space data using zero-filled or sliding window reconstruction and sensitivity maps; decomposing the image space data into a compressed representation comprising a product of spatial and temporal parts, where the spatial part comprises spatial basis functions and the temporal part comprises temporal basis functions; processing the spatial basis functions and temporal basis functions to produce reconstructed spatial basis functions and reconstructed temporal basis functions, wherein the processing iteratively applies conjugate gradient and convolutional neural network updates using 2D or 3D spatial and 1D temporal networks; and decompressing the reconstructed spatial basis functions and reconstructed temporal basis functions to produce a reconstructed MRI image having one or more temporal dimensions and two or more spatial dimensions.

Preferably, the method includes dividing the image space data into image blocks; and decomposing the image space data includes decomposing the image blocks in a block-wise decomposition, wherein the spatial basis functions and temporal basis functions are block-wise spatial basis functions and block-wise temporal basis functions.

DETAILED DESCRIPTION OF THE INVENTION

Reconstruction Overview

In embodiments of the present invention, compressed representations of MRI data are obtained in the form of basis functions. Any data can be represented as a linear combination of a set of basis functions. Often MRI data is redundant, which means that it can be compactly represented by a reduced set of basis functions. Here, this concept is leveraged in spatial and temporal dimensions by decomposing redundant dynamic MRI data into a product of simpler spatial and temporal basis functions. This is known as a globally low-rank (GLR) model, which has been demonstrated to be effective at representing global contrast changes, but not spatially localized dynamics commonly found in cardiac cine images [6]. In another embodiment, known as DSLR+ in this document, a locally low-rank (LLR) model is used to reduce temporal blurring of rapidly moving structures which cannot be captured by the GLR model [7].

Figure 1A:
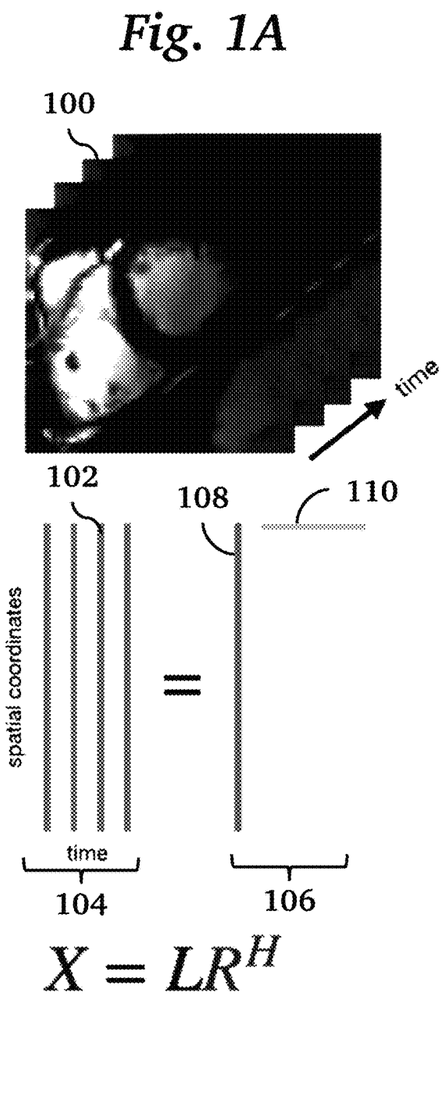
FIGS. 1A and 1B are diagrams that compare alternative low-rank models of image data decomposition, according to embodiments of the invention.
Figure 1B:
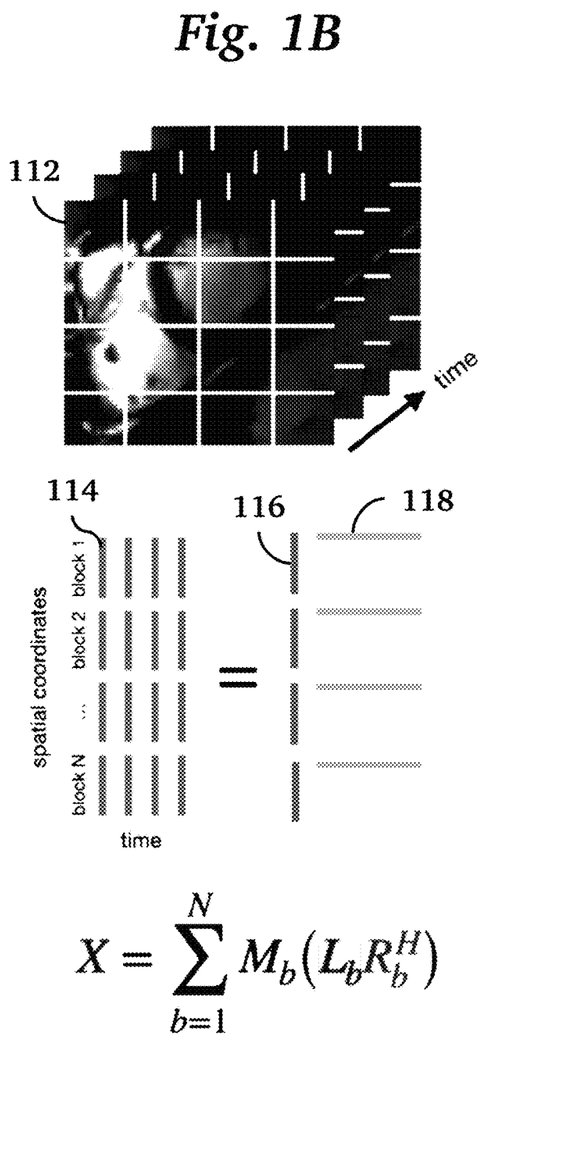

FIGS. 1A and 1B are diagrams that compare these two low-rank models of image data decomposition, according to embodiments of the invention.

In the GLR model shown in FIG. 1A each time frame 100 is vectorized 102 and concatenated to form a 2D matrix 104. The globally low-rank (GLR) model assumes that this matrix X 104 is low-rank and can therefore be represented as a product $LR^H$ 106 of two matrices L 108 and R 110 containing relatively few spatial and temporal basis functions.

The locally low-rank (LLR) model shown in FIG. 1B modifies GLR by exploiting spatially localized low-rank structure. Each time frame image is divided into equally-sized blocks 112, then each block b is vectorized 114 and concatenated to form a 2D matrix $X_b$ which is decomposed into a product $X_b = L_b R_b^H$ of two matrices $L_b$ 116 and $R_b$ 118 containing block-wise spatial and temporal basis functions, respectively. The products $L_b R_b^H$ are summed over all N blocks using operators $M_b$ that convert the blocks back into the image representation. Although non-overlapping blocks are depicted here for simplicity, overlapping blocks are used in this work to reduce blocking artifacts commonly associated with LLR methods.

The matrices $L_b$ and $R_b$, which contain the block-wise basis functions (i.e., derived features), can be jointly estimated by iteratively solving the following non-convex optimization problem:

$$\mathrm{argmin}_{L_b, R_b} \|Y - A\Sigma_b M_b(L_b R_b^H)\|_F^2 \Sigma_b \Psi(L_b) + \Phi(R_b) \quad (1)$$

where Y is the raw k-space data, $M_b$ converts blocks to the image representation, and A is the MRI physics model comprised of coil sensitivity maps, Fourier transform, and k-space sampling mask. Functions $\Psi$ and $\Phi$ are spatial prior and temporal prior regularizers whose proximal operators are modelled by convolutional neural networks (CNNs).

In DSLR, Eq. 1 may be solved by an unrolled alternating minimization (AltMin) approach which alternates between data consistency steps and neural networks evaluated on the block-wise basis functions. In particular, data consistency is mainted for $L_b$ and $R_b$ by gradient descent updates:

$$L_b^{(k+1/2)} = L_b^{(k)} - \alpha_L A^H(Y - A\Sigma_b M_b(L_b^{(k)} R_b^{(k)H})) R_b^{(k)}$$

$$L_b^{(k+1)} = \mathrm{CNN}_{2D}(L_b^{(k+1/2)})$$

$$R_b^{(k+1/2)} = R_b^{(k)} - \alpha_R (Y - A\Sigma_b M_b(L_b^{(k)} R_b^{(k)H}))^H A L_b^{(k)}$$

$$R_b^{(k+1)} = \mathrm{CNN}_{1D}(R_b^{(k+1/2)})$$

where $\alpha_L$ and $\alpha_R$ are step sizes which can either be learned along with other parameters in the network, or dynamically selected using the maximum singular values of $R_b$ and $L_b$ respectively.

In DSLR+, Eq. 1 may be solved by an unrolled AltMin approach which enforces a stronger data consistency for $L_b$ and $R_b$ by inverting the MRI model in each AltMin step:

$$L_b^{(k+1/2)} = \mathrm{argmin}_{L_b} \|Y - A\Sigma_b M_b(L_b R_b^{(k)H})\|_F^2 \quad (2)$$

$$L_b^{(k+1)} = \mathrm{CNN}_{2D}(L_b^{(k+1/2)}) \quad (3)$$

$$R_b^{(k+1/2)} = \mathrm{argmin}_{R_b} \|Y - A\Sigma_b M_b(L_b^{(k)} R_b^H)\|_F^2 \quad (4)$$

$$R_b^{(k+1)} = \mathrm{CNN}_{1D}(R_b^{(k+1/2)}) \quad (5)$$

Since Eq. 2 and 4 are linear with respect to the optimization variables $L_b$ and $R_b$, a globally optimal solution is found by the conjugate gradient (CG) algorithm for each unrolled iteration k.

Figure 1C:
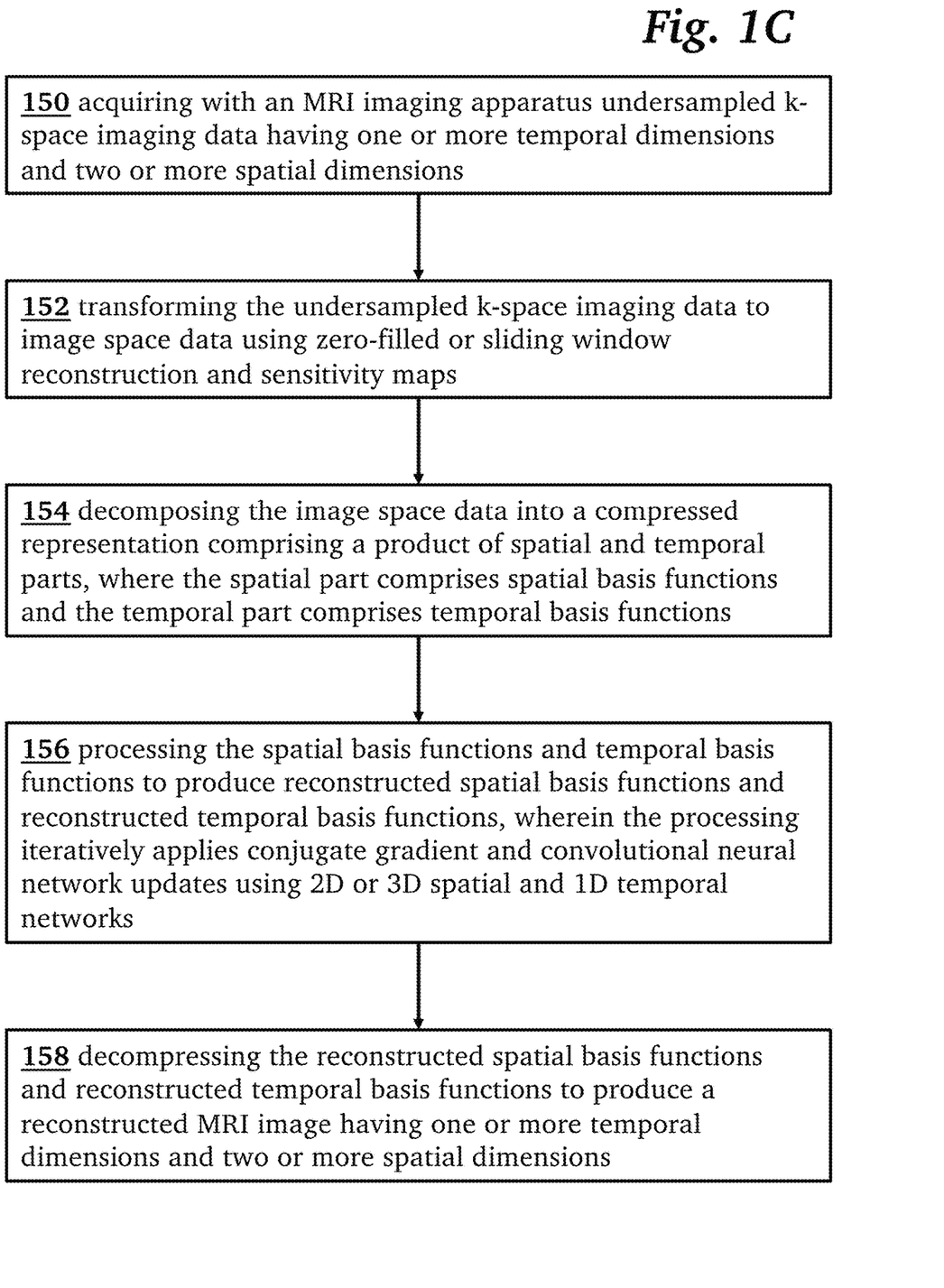
FIG. 1C is a flow chart providing an overview of an MRI image reconstruction method according to an embodiment of the invention.

FIG. 1C is a flow chart providing an overview of an MRI image reconstruction method according to an embodiment of the invention. Step 150 includes acquiring with an MR imaging apparatus undersampled k-space imaging data having one or more temporal dimensions and two or more spatial dimensions. Step 152 includes transforming the undersampled k-space imaging data to image space data using zero-filled or sliding window reconstruction and sensitivity maps. Step 154 includes decomposing the image space data into a compressed representation comprising a product of spatial and temporal parts, where the spatial part comprises spatial basis functions and the temporal part comprises temporal basis functions. In the DSLR+ embodiment, the method includes dividing the image space data into image blocks; and decomposing the image space data includes decomposing the image blocks in a block-wise decomposition, wherein the spatial basis functions and temporal basis functions are block-wise spatial basis functions and block-wise temporal basis functions. Step 156 includes processing the spatial basis functions and temporal basis functions to produce reconstructed spatial basis functions and reconstructed temporal basis functions, wherein the processing iteratively applies conjugate gradient and convolutional neural network updates using 2D or 3D spatial and 1D temporal networks. Step 158 includes decompressing the reconstructed spatial basis functions and reconstructed temporal basis functions to produce a reconstructed MRI image having one or more temporal dimensions and two or more spatial dimensions.

Neural Network Architecture

In the DSLR+ embodiment, the network is formed by unrolling the update equations described above, and training it end-to-end to learn an iterative procedure for reconstructing the block-wise basis functions. The entire network is trained in a supervised fashion using the average L1-loss between the DSLR+ network output and the fully-sampled reference images. The network may be implemented in PyTorch [8], and trained using the Adam optimizer [9].

Figure 2A:
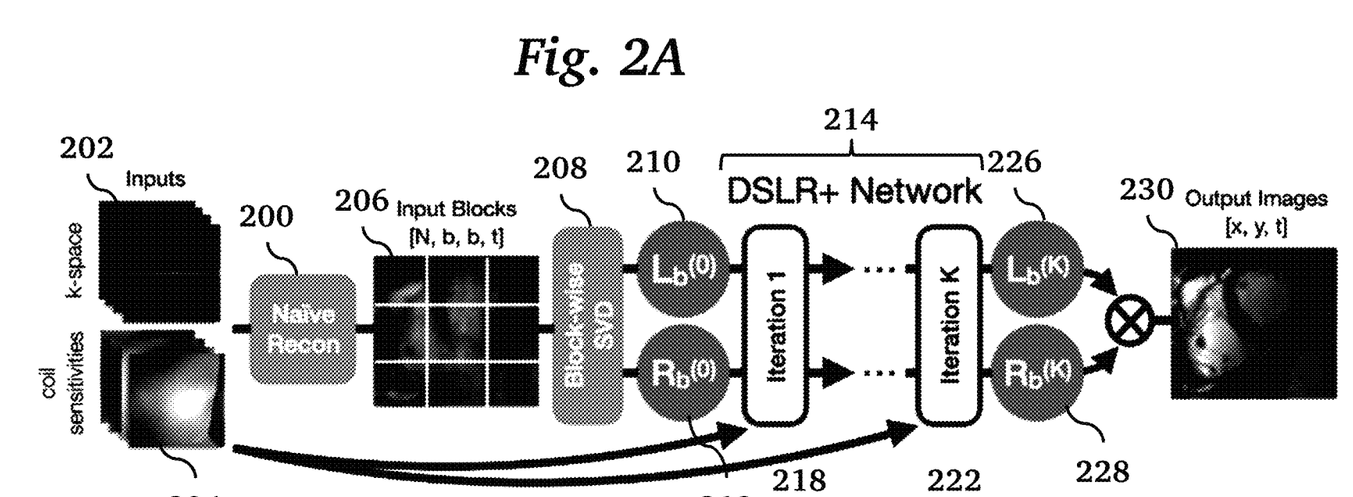
FIGS. 2A and 2B show a network architecture according to an embodiment of the invention.
Figure 2B:
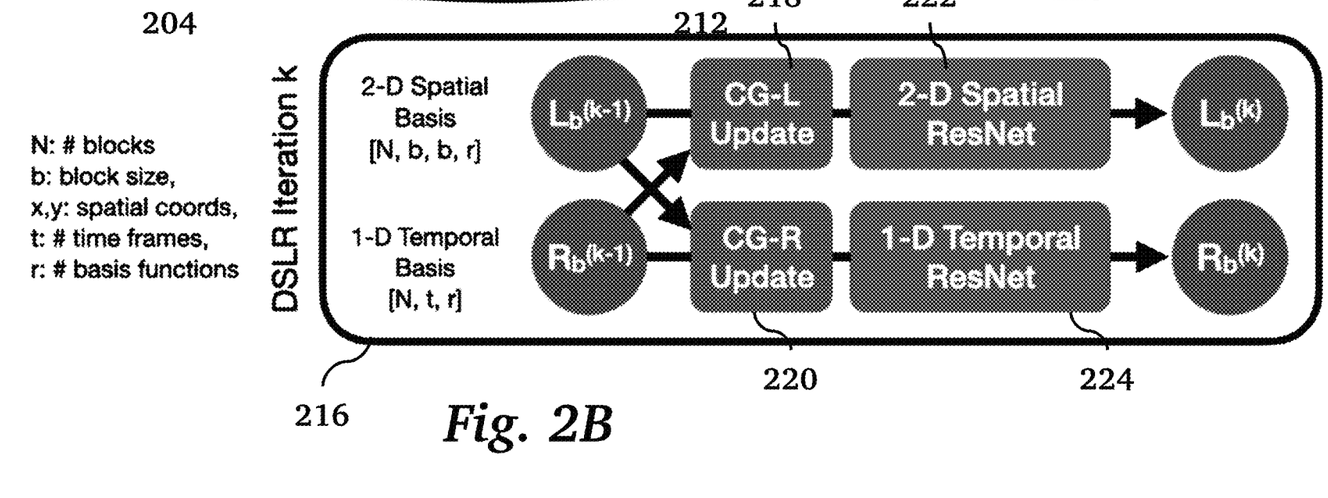

FIGS. 2A and 2B show a DSLR+ network architecture according to an embodiment of the invention. A zero-filled reconstruction 200 is performed on the undersampled k-space data 202 and corresponding sensitivity maps 204 estimated using ESPIRiT. The naive images are then converted into blocks 206, and decomposed using the singular value decomposition (SVD) 208 to initialize the block-wise basis functions, $L_b^{(0)}$ 210 and $R_b^{(0)}$ 212. These complex-valued basis functions are iteratively processed by DSLR+ network 214 composed of K iterations, each iteration 216 containing alternating conjugate gradient (CG) updates 218, 220 and CNN updates 222, 224. Before each CNN, the basis functions are split into real/imaginary components and concatenated along the "feature" dimension. For simplicity, 2D and 1D residual networks (ResNets) 222, 224 comprised of 6 convolutions each are used to model the proximal updates. At the end of the network, the final basis functions $L_b^{(K)}$ 226 and $R_b^{(K)}$ 228 are combined to form the output images 230.

Experiment: Dataset and Training

In an illustrative example, fully-sampled bSSFP 2D cardiac CINE datasets were acquired from 15 volunteers at different cardiac views and slice locations on 1.5 T and 3.0 T GE (Waukesha, WI) scanners using a 32-channel cardiac coil. All datasets were coil compressed [10] to 8 virtual channels for speed and memory considerations. For training, 12 volunteer datasets were split slice-by-slice to create 190 unique cine slices, which were further augmented by random flipping, cropping along readout, and variable-density k-t undersampling (R=10–15). Two volunteer datasets were used for validation, and the remaining dataset was used for testing. One additional prospectively undersampled dataset was collected from a pediatric patient for testing.

We compare three different UNN methods with respect to reconstruction speed and standard image quality metrics (PSNR, SSIM):

1. MoDL [11]: Unrolled half quadratic splitting network with five outer-loop iterations containing 2D+time residual networks [12], 64 features/convolution. Ten inner-loop (CG) iterations are used to perform each model inversion. This network acts on the raw data, and does not perform any sort of compression.
2. DSLR: Unrolled AltMin-PGD network with five iterations containing 2D spatial and 1D temporal residual networks, 256 features/convolution, 8 basis functions, overlapping blocks of size 16×16.
3. DSLR+: Unrolled AltMin-CG network with five outer-loop iterations containing 2D spatial and 1D temporal residual networks, 256 features/convolution, 8 basis functions, overlapping blocks of size 16×16. Ten inner-loop (CG) iterations are used to perform each model inversion.

All networks are trained using the same dataset. Reconstruction benchmarks are performed by reconstructing a test dataset with 200×180 matrix size and 20 cardiac phases on an NVIDIA Titan RTX 24 GB.

Figure 3A:
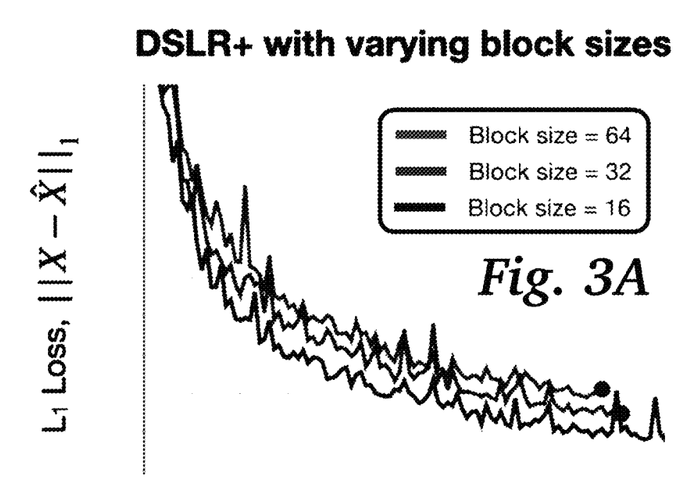
FIGS. 3A, 3B, 3C, 3D are graphs showing validation loss curves for various networks according to an embodiment of the invention.
Figure 3B:
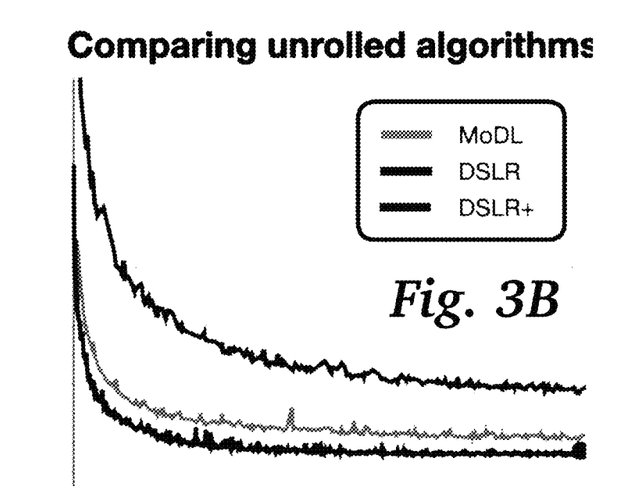
Figure 3C:
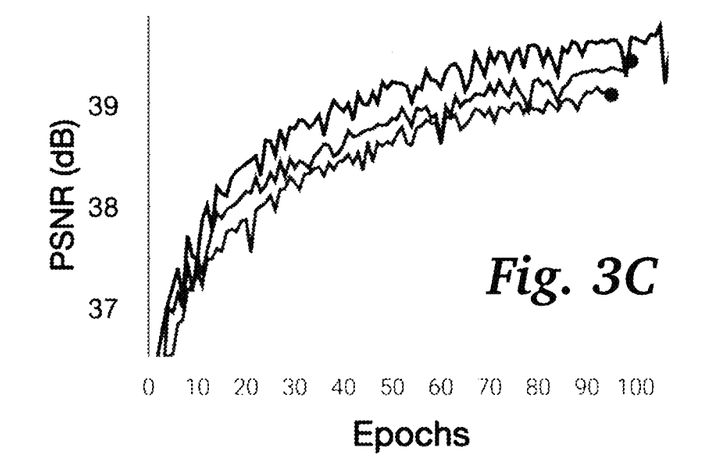
Figure 3D:
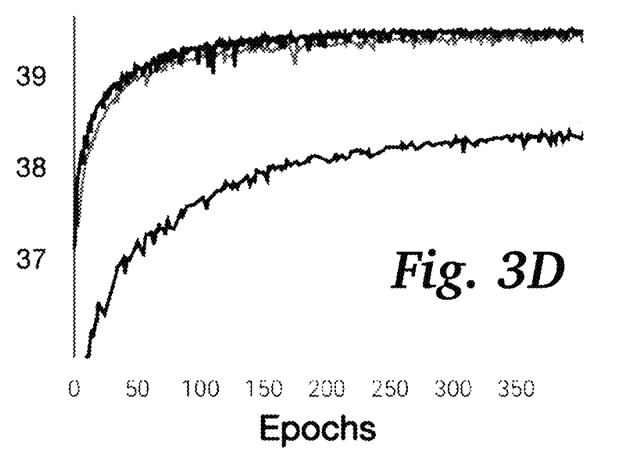

FIGS. 3A, 3B, 3C, 3D are graphs showing validation loss curves for various networks according to an embodiment of the invention. FIGS. 3A, 3C show L1 loss and PSNR evaluated on the validation set training of separate DSLR+ networks with block sizes of 16×16, 32×32, and 64×64. As the block size is decreased, both L1 loss and PSNR are improved. This is because the LLR model has more degrees of freedom to represent the underlying image dynamics as the block size is decreased. FIGS. 3B, 3D show L1 loss and PSNR evaluated on the validation set for MoDL, DSLR, and DSLR+ networks. The DSLR+ network shows significantly better performance on the validation set compared to original DSLR. This suggests that performing model inversion in each unrolled iteration allows the network to converge to a solution quicker than with simpler PGD steps.

Figure 4:
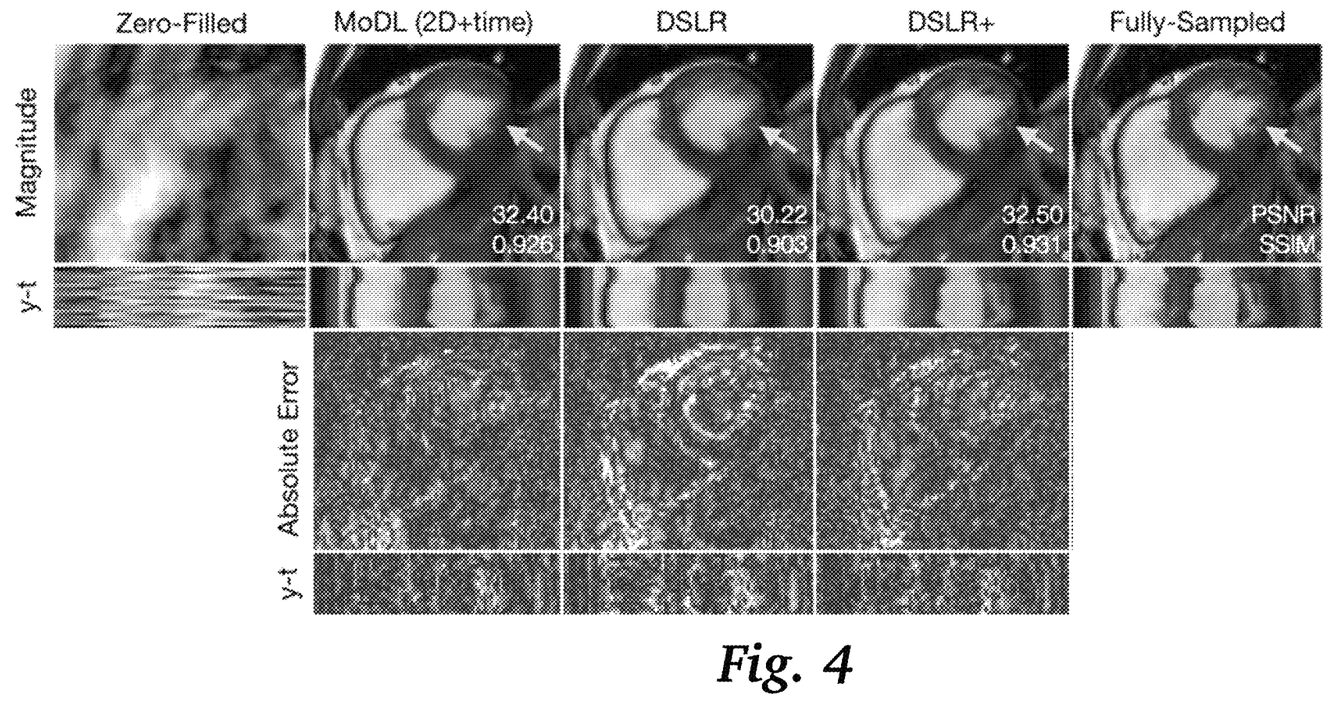
FIG. 4 shows images comparing UNN reconstructions of retrospectively undersampled data according to an embodiment of the invention.

During network training, DSLR+ converges much faster than DSLR, but only slightly faster than MoDL. The average reconstruction times for MoDL, DSLR, and DSLR+ are 1.33+/−0.06, 0.33+/−0.05, and 1.34+/−0.09 sec/slice respectively. The DSLR+ depicts superior image quality in reconstructions of 14 times retrospectively undersampled data compared to both MoDL and DSLR. FIG. 4 shows images comparing UNN reconstructions of retrospectively undersampled data. A fully-sampled dataset is retrospectively undersampled by 14 times using a variable-density k-t sampling pattern. This data is then reconstructed using (from left-to-right): zero-filling, MoDL, DSLR, and DSLR+ methods. Magnitude, errors, and y-t profiles are shown. PSNR and SSIM metrics are computed within an ROI around the heart and displayed on top of magnitude images. The proposed DSLR+ shows superior performance with respect to image quality metrics. Additionally, DSLR+ provides sharper definition of small papillary muscles compared to MoDL and DSLR (indicated by arrows).

Variations and Modifications

It will be appreciated that the techniques described herein are not limited to the specific embodiments described, and that various alternative implementations and embodiments are possible.

For example, different loss functions can be used for training to improve image accuracy and sharpness. These loss functions include SSIM, $\ell_2$ norm, $\ell_1$ norm, and combinations of the different functions. Furthermore, the network can be trained using perceptual or adversarial loss functions.

Embodiments of the invention may use different neural network architectures to reconstruct basis functions. These network architectures can include residual networks (ResNets), U-Nets, autoencoder, recurrent neural networks, and fully connected networks. Individual convolution and activation layers can also be modified to natively support complex-valued data. [13].

Embodiments of the invention may use a modified imaging model, which could incorporate off-resonance information, a signal decay model, k-space symmetry with homodyne processing, and arbitrary sampling trajectories (radial, spiral, hybrid encoding, etc.).

Embodiments of the invention may use techniques other than the singular value decomposition (SVD) to compute the low-rank representation needed as an initial guess for the DSLR network. In this work, we applied this compression to data with two spatial dimensions and one temporal dimension. Importantly, this compression can be generalized to data with even higher dimensions (i.e., low-rank tensor model). This means that the number of weights in the neural network scales linearly with data dimensionality instead of exponentially as with other approaches. Other types of data compression could also be used, such as multi-scale low-rank [14].

REFERENCES

[1] K. P. Pruessmann, M. Weiger, M. B. Scheidegger, and P. Boesiger, "SENSE: Sensitivity encoding for fast MRI," Magnetic Resonance in Medicine, vol. 42, no. 5, pp. 952-962, 1999.

[2] M. A. Griswold, S. Kannengiesser, R. M. Heidemann, J. Wang, and P. M. Jakob, "Field-of-view limitations in parallel imaging," Magnetic Resonance in Medicine, vol. 52, pp. 1118-1126, 2004.

[3] M. Lustig, D. Donoho, and J. M. Pauly, "Sparse MRI: The application of compressed sensing for rapid MR imaging," Magnetic Resonance in Medicine, vol. 58, no. 6, pp. 1182-95, 2007.

[4] K. Hammernik, T. Klatzer, E. Kobler, M. P. Recht, D. K. Sodickson, T. Pock, and F. Knoll, "Learning a variational network for reconstruction of accelerated MRI data," Magnetic Resonance in Medicine, vol. 79, no. 6, pp. 3055-3071, 2018.

[5] C. M. Sandino, P. Lai, S. S. Vasanawala, and J. Y. Cheng, "Accelerating cardiac cine MRI using a deep learning-based ESPIRiT reconstruction," Magnetic Resonance in Medicine, vol. 85, pp. 152-167, January 2021.

[6] Z. P. Liang, "Spatiotemporal imaging with partially separable functions," in Proceedings of the 4th IEEE International Symposium on Biomedical Imaging: From Nano to Macro, 2007.

[7] J. D. Trzasko and A. Manduca, "Local versus global low-rank promotion in dynamic MRI series reconstruction," in Proceedings of the 19th Annual Meeting of the International Society of Magnetic Resonance in Medicine, (Montreal, Quebec, Canada), 2011.

[8] A. Pramanik, H. K. Aggarwal, and M. Jacob, "Deep Generalization of Structured Low-Rank Algorithms (Deep-SLR)," IEEE Transactions on Medical Imaging, vol. 39, pp. 4186-4197, December 2020.

[9] D. P. Kingma and J. L. Ba, "Adam: A method for stochastic gradient descent," ICLR: International Conference on Learning Representations, 2015.

[10] T. Zhang, J. Y. Cheng, Y. Chen, D. G. Nishimura, J. M. Pauly, and S. S. Vasanawala, "Robust self-navigated body MRI using dense coil arrays," Magnetic Resonance in Medicine, vol. 76, no. 1, pp. 197-205, 2015.

[11] H. K. Aggarwal, M. P. Mani, and M. Jacob, "MoDL: Model-Based Deep Learning Architecture for Inverse Problems," IEEE Transactions on Medical Imaging, vol. 38, pp. 394-405, February 2019.

[12] K. He, X. Zhang, S. Ren, and J. Sun, "Deep Residual Learning for Image Recognition," in IEEE Conference on Computer Vision and Pattern Recognition (CVPR), 2016.

[13] P. Virtue, S. X. Yu, and M. Lustig, "Better than real: Complex-valued neural nets for MRI fingerprinting," in International Conference on Image Processing (ICIP), 2018.

[14] F. Ong, X. Zhu, J. Y. Cheng, K. M. Johnson, P. E. Z. Larson, S. S. Vasanawala, and M. Lustig, "Extreme MRI: Large-Scale Volumetric Dynamic Imaging from Continuous Non-Gated Acquisitions," arXiv:1909.13482 [physics], September 2019.

The invention claimed is:

1. A method for MR imaging, the method comprising:
acquiring with an MR imaging apparatus undersampled k-space imaging data having one or more temporal dimensions and two or more spatial dimensions;
transforming the undersampled k-space imaging data to image space data using zero-filled or sliding window reconstruction and sensitivity maps;
decomposing the image space data into a compressed representation comprising a product of spatial and temporal parts, where the spatial part comprises spatial basis functions and the temporal part comprises temporal basis functions;
processing the spatial basis functions and temporal basis functions to produce reconstructed spatial basis functions and reconstructed temporal basis functions, wherein the processing iteratively applies conjugate gradient and convolutional neural network updates using 2D or 3D spatial and 1D temporal networks;
decomposing the reconstructed spatial basis functions and reconstructed temporal basis functions to produce a reconstructed MRI image having one or more temporal dimensions and two or more spatial dimensions.

2. The method of claim 1 further comprising:
dividing the image space data into image blocks;
wherein decomposing the image space data comprises decomposing the image blocks in a block-wise decomposition, wherein the spatial basis functions and temporal basis functions are block-wise spatial basis functions and block-wise temporal basis functions.

3. A method for MR imaging, the method comprising:
acquiring with an MR imaging apparatus undersampled k-space imaging data;
transforming the undersampled k-space imaging data to image space data;
decomposing the image space data into a compressed representation comprising a product of spatial and temporal parts, where the spatial part comprises spatial basis functions and the temporal part comprises temporal basis functions;
processing the spatial basis functions and temporal basis functions to produce reconstructed spatial basis functions and reconstructed temporal basis functions, wherein the processing iteratively applies conjugate gradient and convolutional neural network updates;
decompressing the reconstructed spatial basis functions and reconstructed temporal basis functions to produce a reconstructed MRI image.

* * * * *